US011022599B2

(12) United States Patent
Walden et al.

(10) Patent No.: US 11,022,599 B2
(45) Date of Patent: Jun. 1, 2021

(54) SELF-REGULATING ALCOHOL BREATHALYZER

(71) Applicant: Breathalytics, LLC, St. Paul, MN (US)

(72) Inventors: Ryan Walden, Minneapolis, MN (US); David Kreitzer, Roseville, MN (US)

(73) Assignee: Breathalytics, LLC, St. Paul, MN (US)

( * ) Notice: Subject to any disclaimer, the term of this patent is extended or adjusted under 35 U.S.C. 154(b) by 408 days.

(21) Appl. No.: 16/103,603

(22) Filed: Aug. 14, 2018

(65) Prior Publication Data
US 2019/0056381 A1    Feb. 21, 2019

Related U.S. Application Data

(60) Provisional application No. 62/546,382, filed on Aug. 16, 2017.

(51) Int. Cl.
| | |
|---|---|
| *G01N 33/497* | (2006.01) |
| *H01M 8/04746* | (2016.01) |
| *H01M 8/1018* | (2016.01) |
| *H01M 8/1007* | (2016.01) |
| *H01M 8/04664* | (2016.01) |

(52) U.S. Cl.
CPC .... *G01N 33/4972* (2013.01); *H01M 8/04746* (2013.01); *H01M 8/04671* (2013.01); *H01M 8/1007* (2016.02); *H01M 8/1018* (2013.01)

(58) Field of Classification Search
CPC .......... G01N 33/4972; H01M 8/04746; H01M 8/1007; H01M 8/04671; H01M 8/1018; Y02E 60/50
See application file for complete search history.

(56) References Cited

U.S. PATENT DOCUMENTS

| | | | | |
|---|---|---|---|---|
| 5,426,415 A | * | 6/1995 | Prachar ................ | B60K 28/063 340/576 |
| 7,841,224 B2 | | 11/2010 | Son | |
| 2008/0078232 A1 | * | 4/2008 | Burke .................. | G01N 33/497 73/23.3 |
| 2009/0325639 A1 | * | 12/2009 | Koehn ................. | G01N 1/2273 455/556.1 |
| 2011/0309932 A1 | * | 12/2011 | Arringdale ........... | B60K 28/063 340/539.14 |
| 2013/0281873 A1 | * | 10/2013 | Evans .................... | A61B 5/087 600/532 |

* cited by examiner

*Primary Examiner* — Suman K Nath
(74) *Attorney, Agent, or Firm* — Taft Stettinius & Hollister LLP; Gerald E. Helget

(57) ABSTRACT

A Self-Regulating Alcohol Breathalyzer has a Main Module Enclosure to channel breath evenly to three Fuel-Cell Sensors. Within the Main Module Enclosure are the Main Circuit Board and the Exhaust Fan. When a user blows into the straw, their breath will flow through the Main Air-Flow Channel, Solenoid Pumps are triggered and breath samples are pulled into the Fuel-Cells as the user's air pressure begins to decline. Each Fuel-Cell Sensor has an opening that protrudes into the Main Air Flow Channel and will have access to pull in samples of the breath passing through the channel. After the breath sample is acquired, the three Fuel Cells comparatively test for alcohol content.

14 Claims, 9 Drawing Sheets

SELF-REGULATING ALCOHOL BREATHALYZER

A fuel-cell-operated alcohol breathalyzer has the potential to lose accuracy without obviously detectable indications. When this happens, a breathalyzer may provide skewed test results without the operator being aware of the discrepancy. Inaccuracy can be attributed to either a loss in calibration, or the complete deterioration of the fuel-cell sensor. When a fuel-cell sensor loses calibration, recalibrating the sensor should be able to restore it to an accurate output. A complete deterioration of the fuel-cell is often indicated by little-to-no recognition of the presence of alcohol. In these cases, calibrating the sensor will not restore the accuracy.

Inventors believe there are two ways to diagnose a loss in accuracy. The first way is to use more than one sensor and compare the results. If there is inconsistency in the results of a test, it can be determined that at least one of the sensors has lost calibration. The second way to diagnose a loss in accuracy is to introduce a breath-alcohol-simulating gas (or vapor) with a known alcohol concentration. If the breathalyzer's output is not consistent with the known concentration of the gas or vapor, it can be determined that the sensor has lost accuracy.

To minimize the chances of inaccurate test results, operators of breathalyzers are advised to calibrate devices with enough frequency that loss of accuracy does not occur. However, even if a breathalyzer is calibrated regularly, there is a lack of evidence to confirm that it is accurate at any given time.

Additionally, calibrating a breathalyzer has previously been an expensive procedure because of the manual labor and technical expertise required. To reduce this cost of calibration, other inventions have been developed to simplify the process. For instance, U.S. Pat. No. 7,841,224B2 was issued for a pre-calibrated sensor module, which would negate the inconvenience of bringing calibration equipment to breathalyzers or bring breathalyzers to calibration equipment.

Other inventions have not solved the issue of being able to accurately detect when a breathalyzer has lost calibration, nor have they eliminated the manual labor required to remedy the problem.

With this invention, we have developed a new way to diagnose loss of accuracy and recalibrate a breathalyzer completely automatically, and at a fraction of the cost of other methods.

SUMMARY OF THE INVENTION

A Self-Regulating Alcohol Breathalyzer has a Main Module Enclosure made from a hard plastic, and its primary purpose is to channel breath evenly to three Fuel-Cells Sensors. The Main Module Enclosure acts as a housing unit for several other components, including the Main Circuit Board and the Exhaust Fan. A standard plastic drinking straw is used which users blow into the Breathalyzer. When a user blows into the straw, their breath will flow through the Main Air-Flow Channel. An air-pressure sensor is provided and measures the volume of air passing through the channel and triggers the Solenoid Pumps to activate and pull breath samples into the Fuel-Cells or Fuel Cell Sensors as the user's air pressure begins to decline. The Pressure Sensor is on the Main Circuit Board and will gain access to the Main Air-Flow Channel to measure pressure via a rubber tube. Each fuel-cell sensor has an opening that protrudes into the Main Air Flow Channel and will have access to pull in samples of the breath passing through the channel. Excess breath will continue through the channel and be released through an Air-Flow Exhaust Tube. After the breath sample is acquired, the three Fuel Cells comparatively test for alcohol content. If the three tests are within a margin of error, the test results will be averaged and reported. The Exhaust Fan will activate and push or pull fresh air through the Main Air Flow Channel to expel residual breath and condensation from the area. This mechanism is intended to prevent alcohol residue from affecting the following test result. If the three tests are not within the margin of error, a calibration sequence will be run and a determination of which Fuel Cell Sensors, if any, are defective. Once the defective Fuel Cell Sensor is identified, a re-calibration sequence will be run. If this recalibration is not successful, the particular Fuel Cell Sensor will be disabled.

A self-regulating alcohol breathalyzer has a process that administers an alcohol breath test having at least two Fuel-Cells that each will acquire breath samples for comparative analysis. If the test results are inconsistent, the problem can be immediately identified, automatically triggering a calibration check. The calibration check will identify the Fuel Cell Sensor that has lost accuracy by introducing a gas with a known alcohol concentration. If the discrepancy in the test scores is found to be caused by a loss in calibration, the sensor will be automatically recalibrated. If the problematic Sensor has deteriorated beyond the point of recalibration, the Breathalyzer will be automatically disable the Sensor and prompt a replacement with a digital notification.

A principle object and advantage of the present invention is that all test results, calibration checks and recalibrations will be documented in a database as proof of quality control and to show empirical evidence that our breathalyzer was accurate at any given time, while eliminating the manual labor cost of recalibrating each breathalyzer.

Another object and advantage of the present invention is that it provides the ability to replace Fuel Cell Sensors without the need for any tools and domain expertise. While other breathalyzer designs require precise procedures to properly replace a Fuel Cell, the present breathalyzer can perform this function with non-technical operators replacing fuel cells in a non-controlled environment, without the risk of corrupting or damaging the unit in any way.

COMPONENT PARTS

1A) Fuel-Cell Cartridge 1
1B) Fuel-Cell Cartridge 2
1C) Fuel-Cell Cartridge 3
2) Main Module Enclosure
3) Main Circuit Board
4) Exhaust Fan
5) Straw Entry Funnel
6) Main Air-Flow Channel
7) Air-Flow Exhaust Tube
8) Fuel-Cell Cartridge Circuit Board
9) Fuel-Cell Cartridge Card-Edge Connector
10A) Fuel-Cell
10B) Fuel-Cell Entry Point or Tube
11) Solenoid Pump
12A) Fuel-Cell Cartridge Card-Edge Receptacle 1
12B) Fuel-Cell Cartridge Card-Edge Receptacle 2
12C) Fuel-Cell Cartridge Card-Edge Receptacle 3
E Ears
P Pins
13A) Fuel-Cell Entry Point 1
13B) Fuel-Cell Entry Point 2

13C) Fuel-Cell Entry Point 3
14) Calibration Gas Tube Entry
T Calibration Gas Tube
0 Pressure Sensor
15) Calibration Gas Channel
16A) Calibration Gas Entry Point 1 (same as 13A)
16B) Calibration Gas Entry Point 2 (same as 13B)
16C) Calibration Gas Entry Point 3 (same as 13C)
17) Calibration Gas Canister
18) Calibration Gas Solenoid Valve & Regulator
19) Calibration Gas Connector Tube
20) Standard Plastic Straw
21) Fuel Cell Status LED
22) PCB Mounted Connectors

DETAILED DESCRIPTION

FIGS. 1 to 7 depict overhead views of the Main Module Enclosure 2, without several connecting components to illustrate the general framework of the device. The Main Module Enclosure 2 is made from a hard plastic, and its primary purpose is to channel breath evenly to the 3 Fuel-Cells 10A. Additionally, the Main Module Enclosure 2 acts as a housing unit for several other components, including the Main Circuit Board 3 and the Exhaust Fan 4. A standard plastic drinking straw 20 is used with the apparatus with which users blow into the device. FIGS. 1, 2, 8, and 9 illustrate how a straw 20 is placed into the Main Module Enclosure 2 through the Straw Entry Funnel 5. When a user blows into the straw, their breath will flow through the Main Air-Flow Channel 6. An air-pressure sensor 0 measures the volume of air passing through the channel and triggers the Solenoid Pumps 11 to activate and pull breath samples into the Fuel-Cells or Sensors 10A right as the user's air pressure begins to decline. The Pressure Sensor 0 will be on the Main Circuit Board 3 and will gain access to the Main Air-Flow Channel 6 through a Calibration Gas Tube T to measure pressure through the Pressure Sensor 0 Orifice. Each Fuel-Cell or Sensor 10A has a tubular opening 10B that protrudes into the Main Air Flow Channel 6 and will have access to pull in samples of the breath passing through the channel 6. Excess breath will continue through the channel 6 and be released through the Air-Flow Exhaust Tube 7. After the breath sample is acquired, the Exhaust Fan 4 will activate and push or pull fresh air through the Main Air Flow Channel 6 to expel residual breath and condensation from the area. This mechanism is intended to prevent alcohol residue from affecting the following test result.

Figure 1:
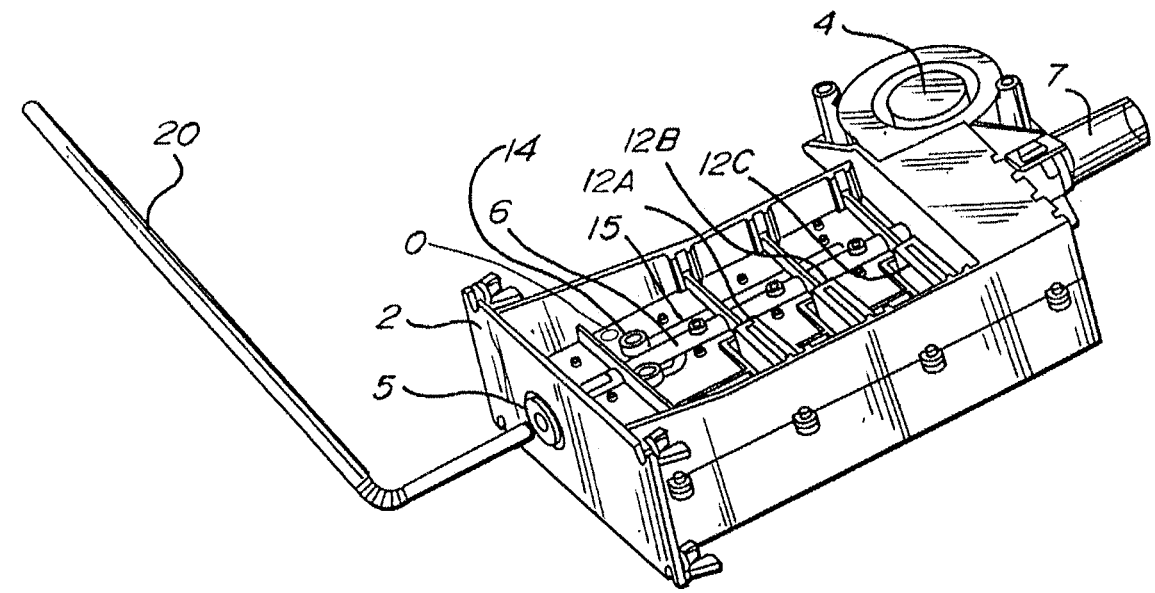
FIGS. 1 and 2 depict overhead views of the Main Module Enclosure 2, without several connecting components to illustrate the general framework of the device.
Figure 2:
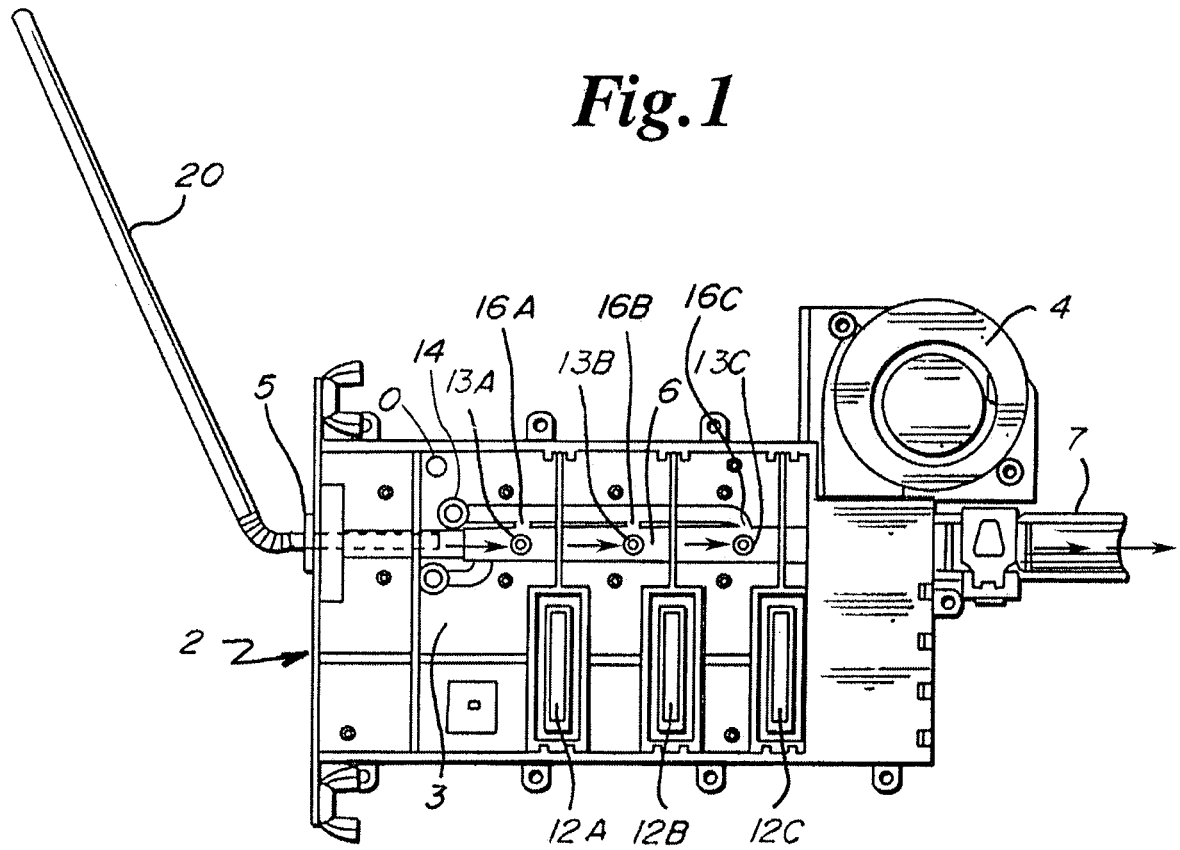
Figure 3:
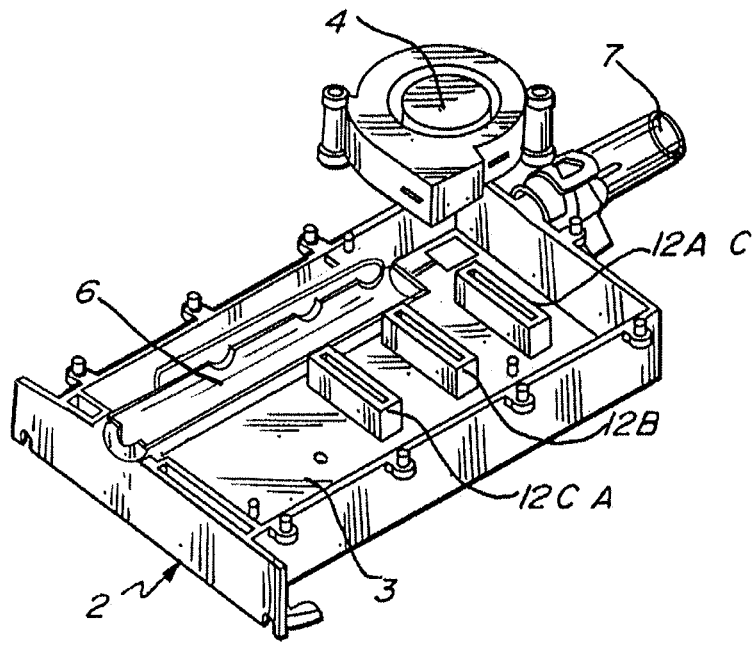
FIG. 3 provides another overhead view of the Main Module Enclosure (2) with the top half of the plastic enclosure stripped away.

FIG. 3 provides another perspective overhead view of the Main Module Enclosure 2 with the top half of the plastic enclosure stripped away. This allows for a clear view of the positioning of the Main Circuit Board 3 as well as the Main Air Flow Channel 6.

Figure 4:
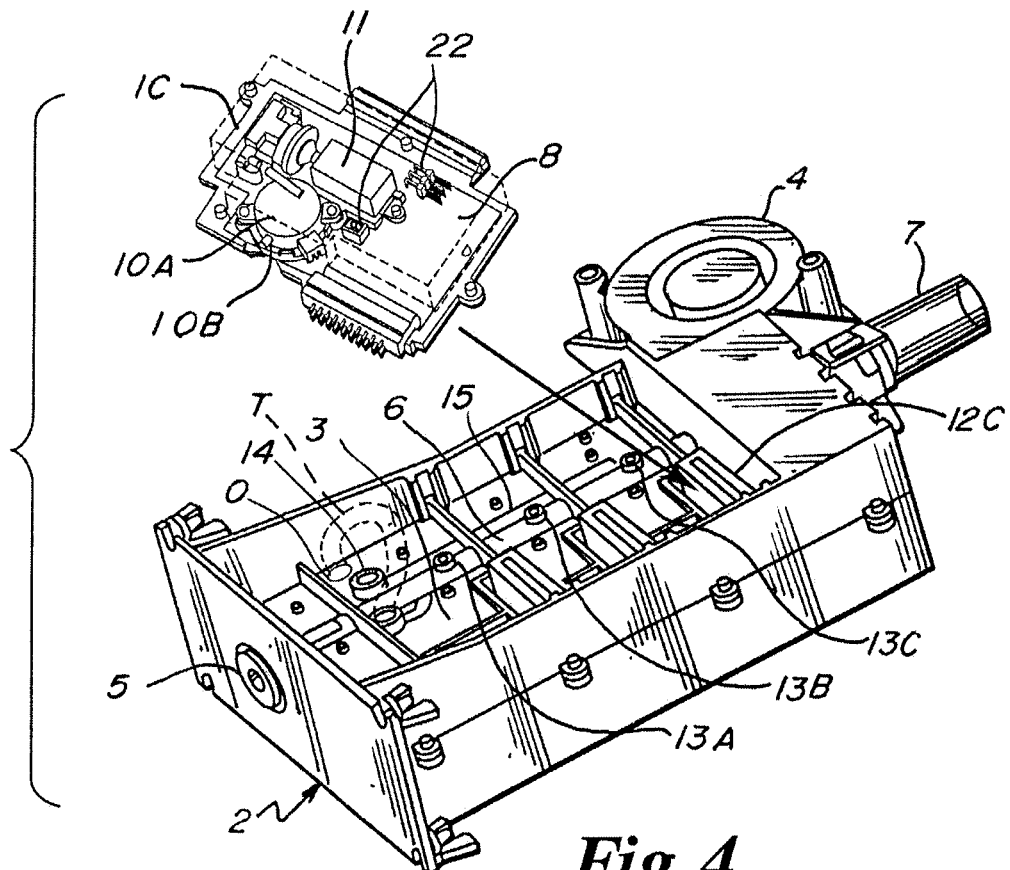
FIG. 4 depicts a Fuel-Cell Cartridge and the main module enclosure.
Figure 5:
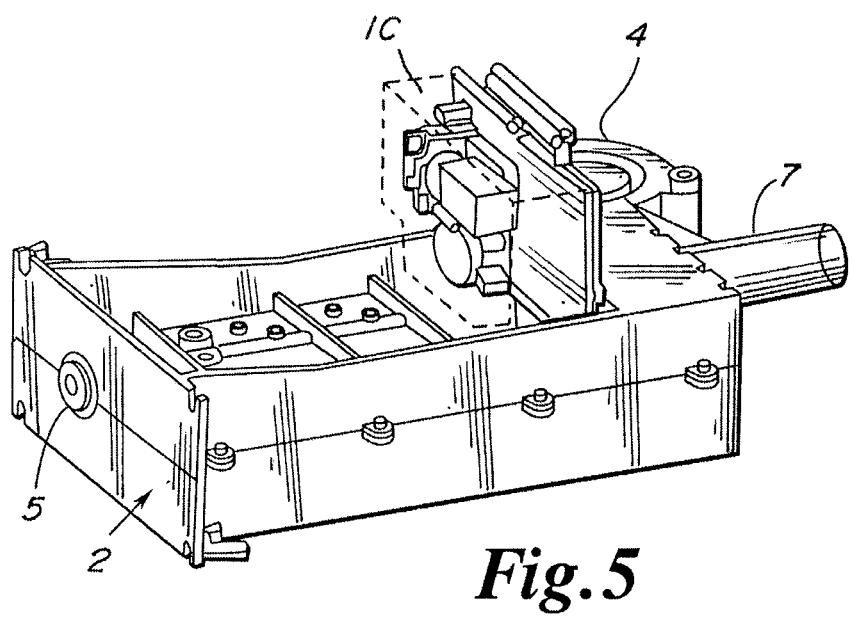
FIG. 5 depicts the Main Module Enclosure with the $3^{rd}$ fuel-cell cartridge installed.
Figure 6:
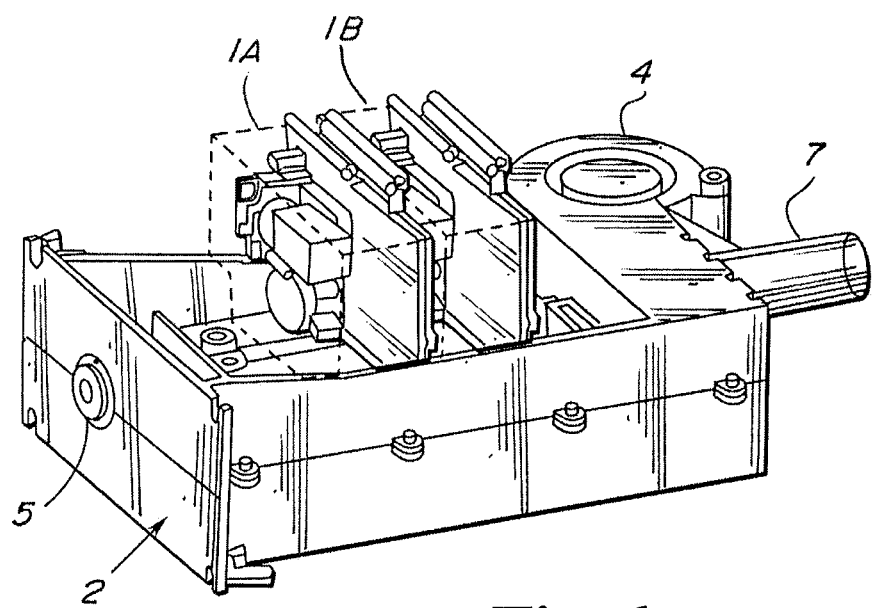
FIG. 6 depicts the Main Module Enclosure with Fuel-Cell Cartridges in the $1^{st}$ and $2^{nd}$ Fuel-Cell Cartridge Card Edge Receptacle.
Figure 7A:
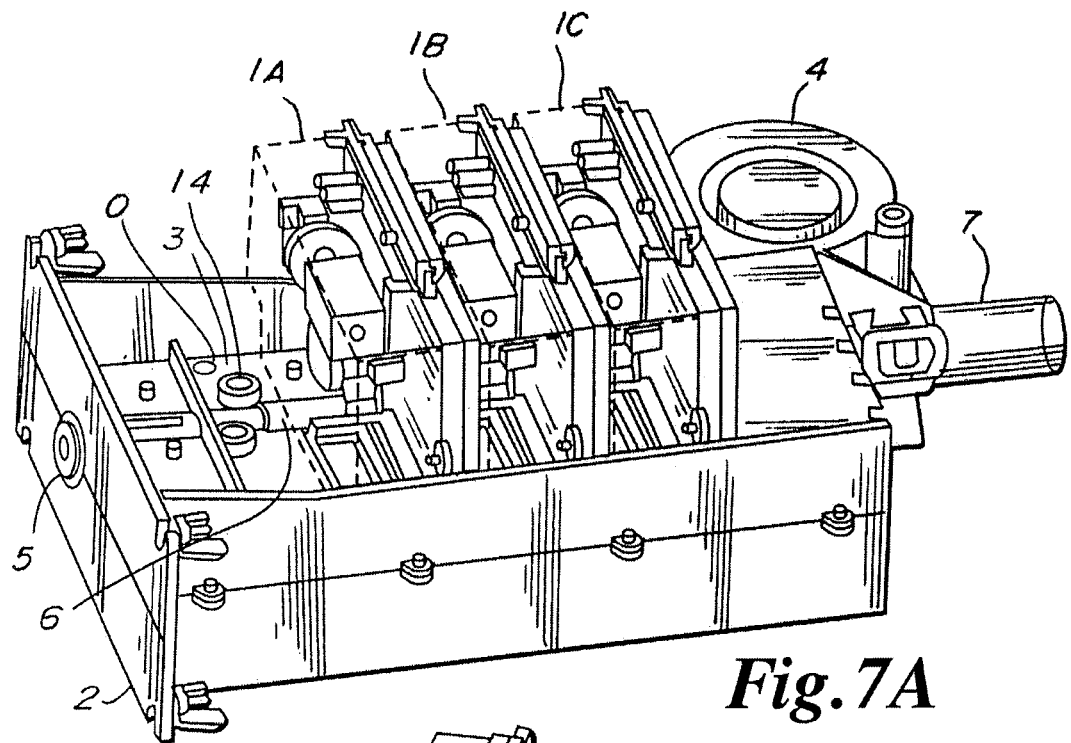
FIG. 7A depicts the Main Module Enclosure with Fuel-Cell Cartridges in all 3 of the Fuel-Cell Cartridge Card Edge Receptacles.
Figure 7B:
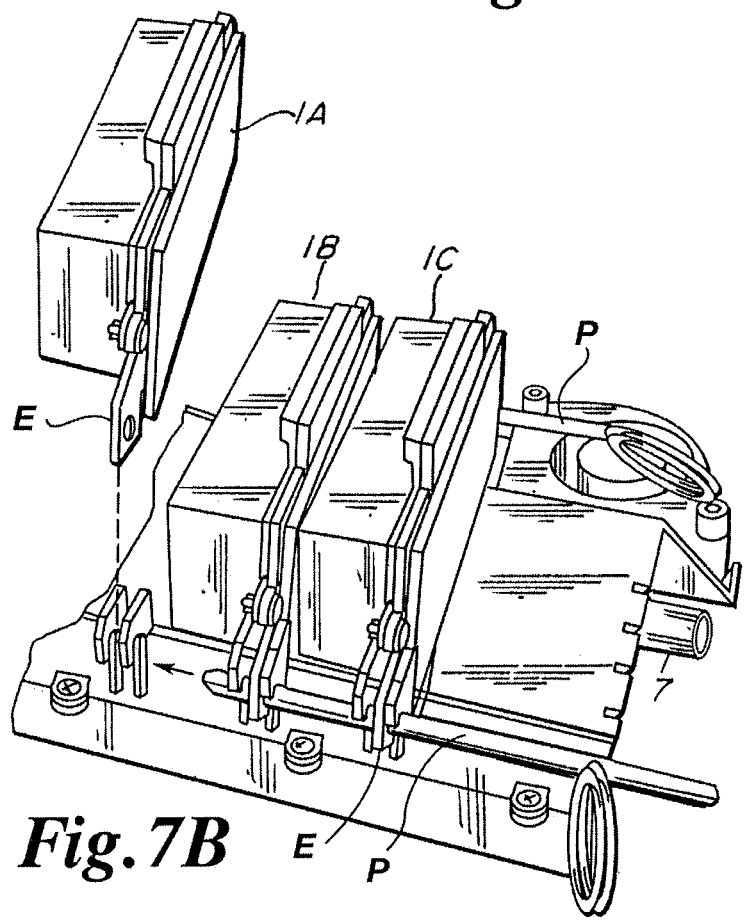
FIG. 7B depicts a locking arrangement of Ears and Pins to secure the Fuel-Cell Cartridges into the Enclosure.
Figure 8:
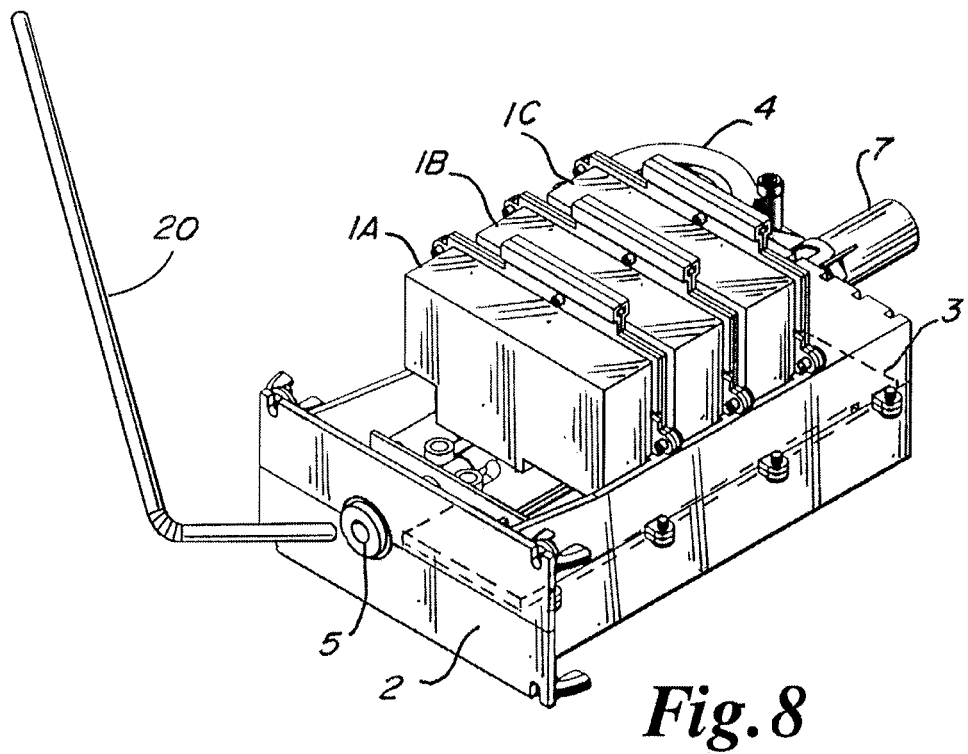
FIGS. 8 and 9 illustrate the Main Module Enclosure with all 3 Fuel-Cell Cartridges installed. These figures also demonstrate the motion of inserting the straw into the Straw Entry Funnel.
Figure 9:
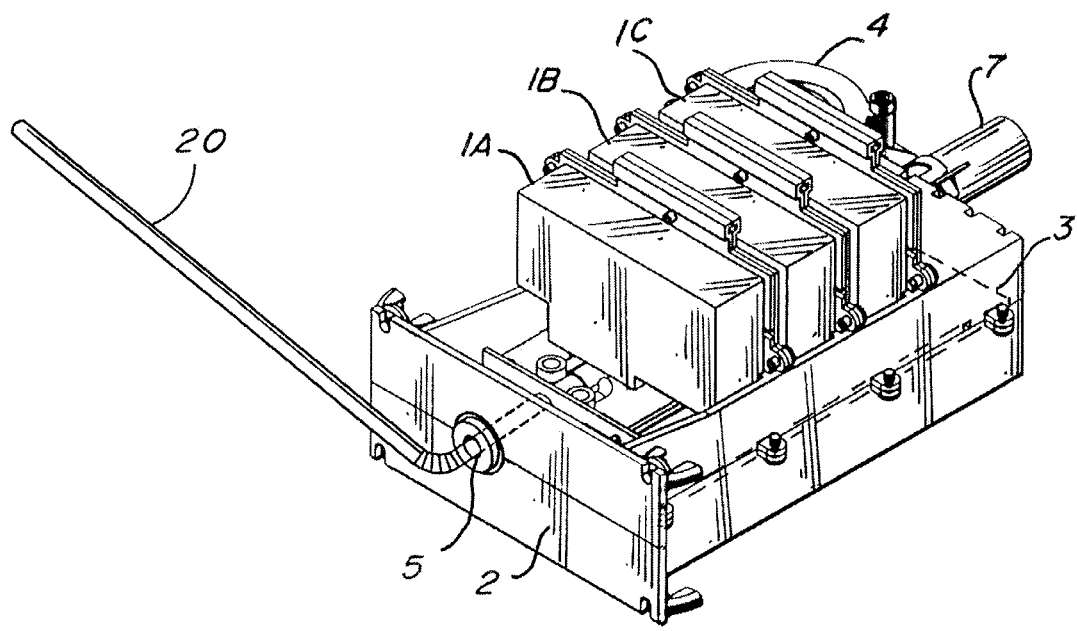

FIGS. 4, 5, 6 and 7A illustrate the process of adding Fuel Cell Cartridges 1A, 1B and 1C (collectively 1) to the Main Module Enclosure 2. FIG. 4 depicts a Fuel-Cell Cartridge 1, with a transparency effect, as it is positioned to be connected to the Fuel-Cell Cartridge Card Edge Receptacle 12C (receptacles 12A, 12B and 12c collectively 12). FIG. 5 depicts the Main Module Enclosure 2 after a Fuel-Cell Cartridge 1 has been placed in the Fuel-Cell Cartridge Card Edge Receptacle 12. For comparison, FIG. 6 depicts the Main Module Enclosure 2 with Fuel-Cell Cartridges 1 in the $1^{st}$ and $2^{nd}$ Fuel-Cell Cartridge Card Edge Receptacle 12. FIG. 7A depicts the Main Module Enclosure 2 with Fuel-Cell Cartridges 1 in all 3 of the Fuel-Cell Cartridge Card Edge Receptacles 12. FIG. 7B depict a locking arrangement of Ears E and Pins P to secure the Fuel-Cell Cartridges into the Enclosure. FIGS. 8 and 9 illustrate the Main Module Enclosure 2 with all 3 Fuel-Cell Cartridges 1 installed. These figures also demonstrate the motion of inserting the straw 20 into the Straw Entry Funnel 5.

Figure 10:
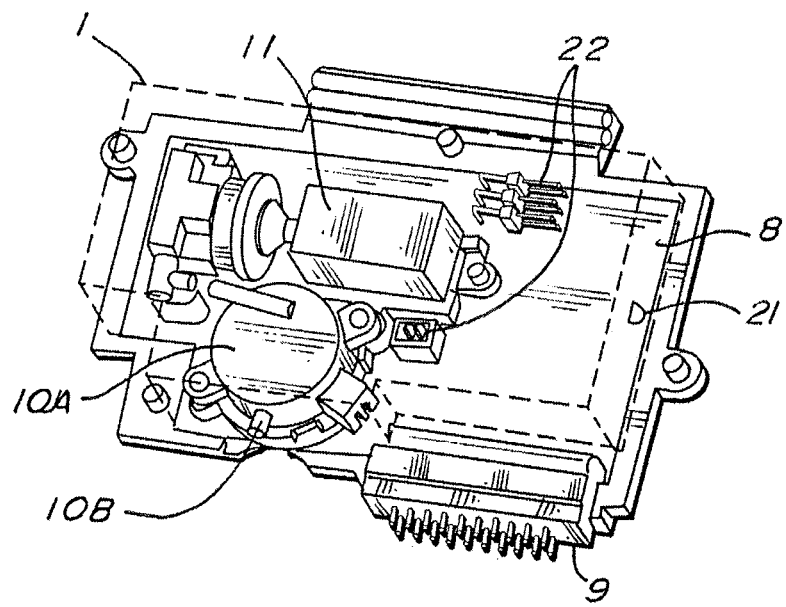
FIGS. 10 and 11 provide a close look at the insides of the Fuel-Cell Cartridge and within the Fuel-Cell Cartridge is the Fuel-Cell and Solenoid Pump, both attached to a Fuel-Cell Cartridge Circuit Board.
Figure 11:
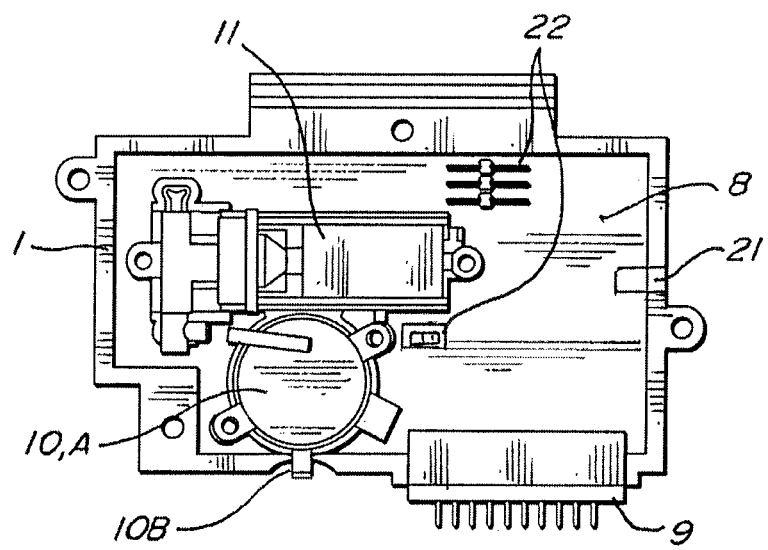

FIGS. 10 and 11 provide a close look at the insides of the Fuel-Cell Cartridge 1 with a transparency effect. Within the Fuel-Cell Cartridge 1 is the Fuel-Cell 10A and Solenoid Pump 11, both attached to a Fuel-Cell Cartridge Circuit Board 8. The Fuel-Cell 10 and Solenoid Pump 11 transfer signals to and from the Fuel Cell Cartridge Circuit Board 8 through PCB-mounted connectors 9, which then connect to the Main Circuit Board 3 through card-edge connectors 12. At the bottom of the Fuel-Cell 10A, there is an opening 10B that protrudes outside the Fuel-Cell Cartridge 1 and into the Main Air Flow Channel 6 to gain access to the breath. The Fuel Cell Connector 9 at the base of the Fuel-Cell Cartridge 1 communicates with the Main Circuit Board (3) via the Fuel-Cell Cartridge Card-Edge Receptacle 12. This plug connector also acts as a way to secure the Fuel Cell Cartridge 1 to the Main Module Enclosure 2.

Figure 12:
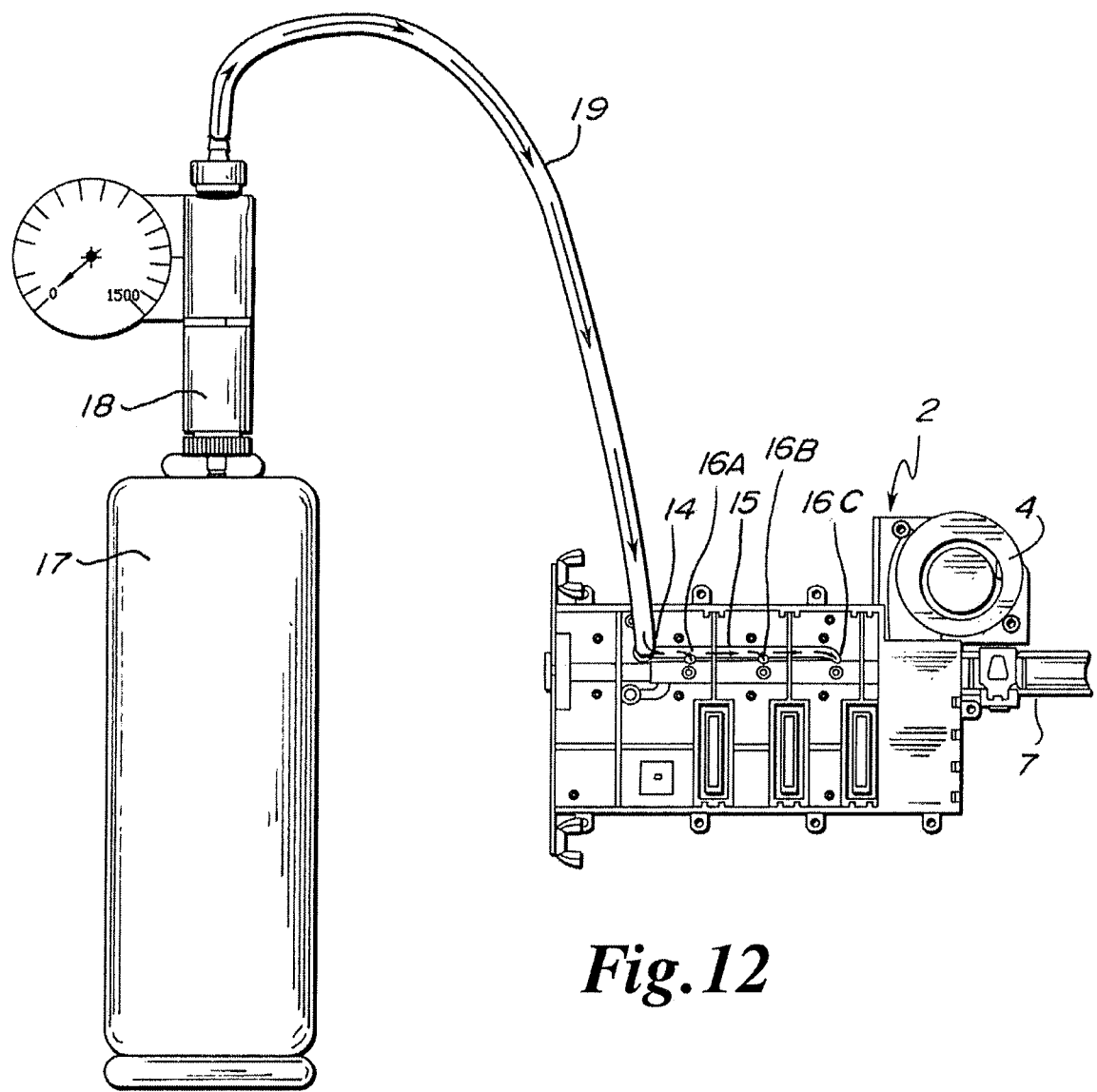
FIG. 12 illustrates the process of the Calibration Gas Canister sending calibrated Ethanol Alcohol Gas into the Main Module Enclosure.

FIG. 12 illustrates the process of the Calibration Gas Canister 17 sending calibrated Ethanol Alcohol Gas into the Main Module Enclosure 2. While other breathalyzers are calibrated by introducing calibration gas through the same entry point as the user's mouthpiece, this design allows for the calibration gas to enter the Main Air Flow Channel 6 through a different entry point to enable remote calibration. The Calibration Gas Connector Tube 19 runs from the Calibration Gas Solenoid Valve & Regulator 18 to the Calibration Gas Tube Entry 14. Once channeled into the Calibration Gas Tube Entry 14, the gas will follow the Calibration Gas Channel 15 to 3 separate outlets 16A, 16B and 16C (collectively 16) that spill into the Main Air-Flow Channel 6. These 3 ports are each aligned with one of the Fuel-Cell Cartridges 1, allowing for even distribution of the calibration gas to all Fuel-Cells 10.

The Calibration Gas Solenoid Valve and Regulator 18 is programmable to release gas at a pre-defined rate and for the duration that it's directed by the Main Circuit Board 3. The Calibration Gas Solenoid Valve and Regulator 18 is connected to the Main Circuit Board 3, and the Main Circuit Board 3 controls the activity of the Calibration Gas Solenoid Valve & Regulator 18 to synchronize with the Fuel-Cells 10 & Solenoid Pumps 11.

During a calibration check, the Calibration Gas Solenoid Valve and Regulator 18 will release gas for several seconds, filling the Main Air-Flow Channel 6 with a sufficient concentration of the gas. Once this concentration is reached, each of the Fuel-Cells 10 will take a sample, and the Main Circuit Board 3 will generate a result. The results will be compared to the known alcohol concentration of the gas to determine if any of the Fuel-Cells are out of calibration. If any of the Fuel-Cells are found to be out of calibration, a recalibration sequence will be triggered. Once again, the Calibration Gas Solenoid Valve and Regulator 18 will release gas into the Main Air-Flow Channel 6 and the problematic fuel-cell will take a sample of the gas. The Fuel-Cell will then reset its calibration settings based on the outcome of the calibration.

Regular calibration intervals will be scheduled to occur automatically, however a calibration sequence can be spontaneously triggered in the event that a discrepancy is detected between 2 or more of the Fuel-Cell test results. Each test taken will result in at least 2 of the Fuel-Cells taking samples. Upon interpreting the BAC (blood alcohol concentration) scores from the Fuel-Cells, the results will be compared for consistency. If the results from the various Fuel-Cells are consistent, within a small standard deviation, they will be accepted as accurate. If the results vary beyond the standard deviation, an automatic calibration check will be triggered. The calibration check will determine if any of the Sensors were accurate at the time of the test, and the results yielded from that sensor(s) will be accepted. In the event that all Fuel-Cells 10 are found to be inaccurate from the calibration check, the test will be flagged as inconclusive.

The hardware depicted in FIGS. 1-12 will be accompanied by a firmware program that runs the commands of the Main Circuit Board 3.

In this design, the Main Circuit Board 3 will also be connected to a computer via a USB port. The computer and Main Circuit Board 3 will be able to exchange data, and a custom software installed on the computer will allow us to remotely operate the device.

Considering various embodiments, the Main Circuit Board 3 consists of a custom Firmware written in C and sensors to read electrical current, temperature, humidity and pressure; is powered by a 12V power source, has a USB 2.0 port to communicate with an external computer and has low voltage connections to operate an electrical solenoid valve which controls the flow of calibration gas to the Main Module Enclosure 2. The Main Air-Flow Channel 6 is the area where air passes underneath the Fuel Cells 10A and allows for the Fuel Cells to apprehend samples of whatever is passing through. The Main Module Enclosure 2 encompasses two separate plastic pieces that connect together and enclose the Main Circuit Board 3. Both plastic pieces can be produced via 3D Printing, Injection Molding, Blow Molding or Plastic Machining.

The FUS Fuel-Cell Cartridge 1 is a plastic enclosure containing a Fuel-Cell Cartridge Circuit Board 8, a Fuel-Cell 10 with a heater to control temperature, and a 5v Solenoid Pump 11. The Main Circuit Board 3 has three exposed Fuel-Cell Cartridge Card-Edge Receptacles 12 which pair with Fuel-Cell Cartridge Card-Edge Connectors 9.

The Calibration Gas Channel 15 has a Calibration Gas Tube Entry 14 that allows for a quick connect fitting for a 3 mm ID Clearflo Connector Tube 19 to securely connect to the Calibration Gas Solenoid Valve & Regulator 18 to deliver Dry Ethanol Calibration Gas to the FUS during calibration cycles. The Air-Flow Exhaust Tube 7 has a quick connect fitting for a ¼" ID Poly Tube to securely connect to the Main Module Enclosure 2 to control the exhaust of calibration gas, human breath and moisture away from the FUS.

The Main Circuit Board 3 has been designed to log electrical current output from the Fuel-Cell Cartridges 1 and has a Temperature Sensor, Pressure Sensor and Humidity Sensor to analyze the Main Air-Flow Channel 6 during test sequences. The Main Circuit Board will run Test Sequences using 1, 2, or 3 installed Fuel-Cell Cartridges 1; Calibration Test Sequences using 1, 2 or 3 installed Fuel-Cell Cartridges 1; and/or Re-Calibration Sequences using 1, 2, or 3 installed Fuel-Cell Cartridges 1.

The Main Circuit Board has a custom Firmware and API allowing communication and commands with a Computer.

The FUS can properly operate with 1, 2, or 3 Fuel-Cell Cartridges 1.

The Fuel-Cell Cartridges 1 can be easily removed and installed by removing the Pins and sliding the Fuel-Cell Cartridge Card-Edge Connector 9 into the Fuel-Cell Cartridge Card-Edge Receptacle 12 without the aid of any tools. The Fuel-Cell Cartridge 1 is held in place by the exposed Fuel-Cell Cartridge Card-Edge Receptacle 12 resting on the Main Module Enclosure 2 with the aid of the Ear and Pin arrangement.

Figure 13:
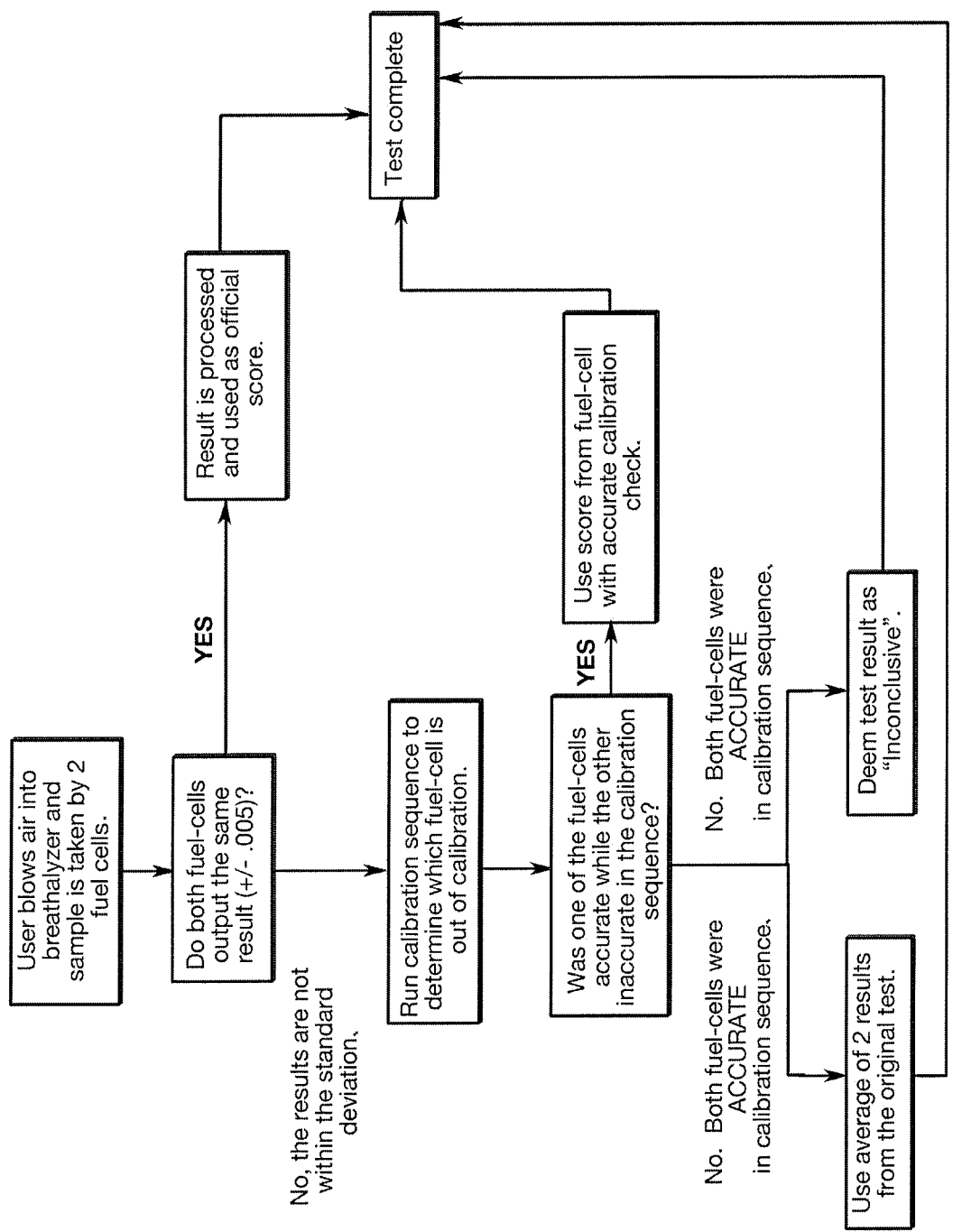
FIG. 13 is a flow chart of the standard test sequence and decision making protocol.

In FIG. 13, the purpose of this flowchart is to illustrate how our system will determine which test result is most reliable in the event that a discrepancy occurs between 2 fuel-cells interpreting the same air sample.

Figure 14:
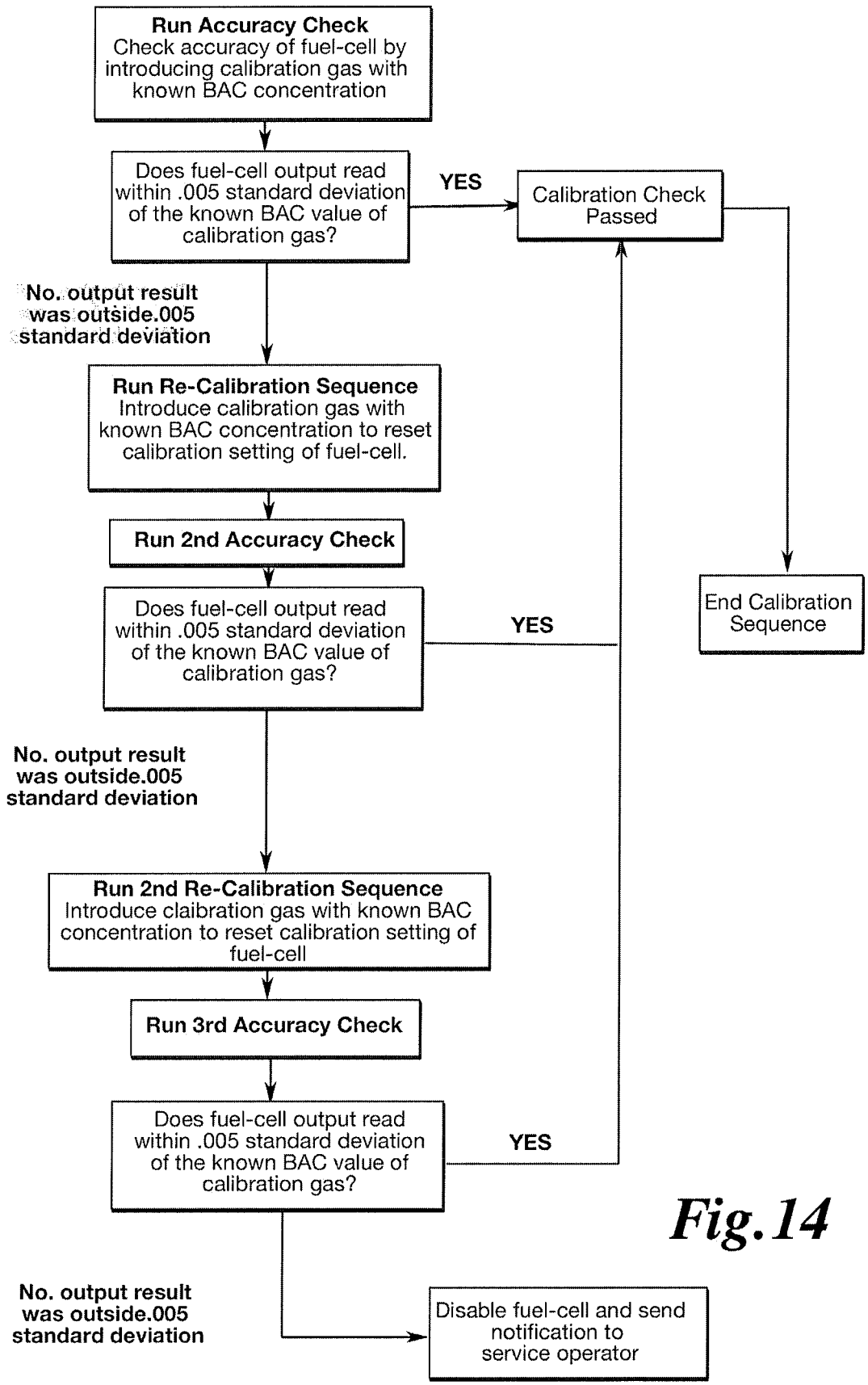
FIG. 14 is a flow chart of Calibration Sequence and Decision Making Protocol.

In FIG. 14, the purpose of this flowchart is to illustrate how our system will check for calibration accuracy and react to situations where one or more fuel-cells are not outputting accurate results.

The terminology used herein is for the purpose of describing particular embodiments only and is not intended to be limiting of the invention. Unless otherwise defined, all terms used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases, all of the other disclosed techniques. Accordingly, for the sake of clarity, this description will refrain from repeating every possible combination of the individual components in an unnecessary fashion. Nevertheless, the specification and claims should be read with the understanding that such combinations are entirely within the scope of the invention and the claims.

Specific details have been set forth about our design and processes to provide a thorough understanding of the present invention. It will be evident, however, to one skilled in the art of making breathalyzers that the benefits derived from our innovations, in the present invention, may also be achieved without using the exact specifications herein disclosed. The present disclosure is to be considered as an exemplification of the invention, and is not intended to limit the invention to the specific embodiments illustrated by the figures or descriptions below.

The invention claimed is:

1. A self-regulating, multi-fuel-cell breathalyzer, comprising:
   a) a main module with a main air-flow channel, a main circuit hoard with a software having first multiple card-edge connectors and an air-pressure sensor in flow communication with the main air-flow channel; and
   b) multiple fuel-cell cartridges each having a fuel-cell sensor, a pump, a fuel-cell sensor intake in flow communication with the main air-flow channel and a second multiple card-edge connector connectable to one of the main module first multiple card-edge connectors, whereby, if one of the fuel-cell sensors is identified as having a loss in calibration, the software performs automatic recalibration of the one of the fuel-cell sensors that has lost calibration and disable the one of the fuel-cell sensors that cannot be automatically recalibrated.

2. The self-regulating, multi-fuel-cell breathalyzer of claim 1, further comprising an exhaust fan to pull or push fresh air through the main air-flow channel.

3. The self-regulating, multi-fuel-cell breathalyzer of claim 1 wherein the multiple fuel-cell cartridges comprise at least two fuel-cell cartridges.

4. The self-regulating, multi-fuel-cell breathalyzer of claim 1 wherein the multiple fuel-cell cartridges comprise at least three fuel-cell cartridges.

5. The self-regulating, multi-fuel-cell breathalyzer of claim 1 further comprising a calibration gas entry in flow communication with the main air-flow channel and a regulated calibration gas source.

6. The self-regulating, multi-fuel-cell breathalyzer of claim 1 further comprising a computer connectable to the main circuit board.

7. A self-regulating, multi-fuel-cell breathalyzer, comprising:
   a) a main module with a main air-flow channel, a main circuit board with a software having first multiple card-edge connectors, an exhaust fan to pull or push fresh air through the main air-flow channel and an air-pressure sensor in flow communication with the main air-flow channel; and
   b) at least two fuel-cell cartridges each having a fuel-cell sensor, a pump, a fuel-cell sensor intake in flow communication with the main air-flow channel and a second multiple card-edge connector connectable to one of the main module first multiple card-edge connectors, whereby, if one of the fuel-cell sensors is identified as having a loss in calibration, the software performs automatic recalibration of the one of the fuel-cell sensors that has lost calibration and disable the one of the fuel-cell sensors that cannot be automatically recalibrated.

8. The self-regulating, multi-fuel-cell breathalyzer of claim 7 wherein the multiple fuel-cell cartridges comprise at least three fuel-cell cartridges.

9. The self-regulating, multi-fuel-cell breathalyzer of claim 7 further comprising a calibration gas entry in flow communication with the main air-flow channel and a regulated calibration gas source.

10. The self-regulating, multi-fuel-cell breathalyzer of claim 7 further comprising a computer connectable to the main circuit board.

11. A self-regulating, multi-fuel-cell breathalyzer, comprising:
    a) a main module with a main air-flow channel, a main circuit board with a software having first multiple card-edge connectors, an exhaust fan to pull or push fresh air through the main air-flow channel and an air-pressure sensor in flow communication with the main air-flow channel; and
    b) at least three fuel-cell cartridges each having a fuel-cell sensor, a pump, a fuel-cell sensor intake in flow communication with the main air-flow channel and a second multiple card-edge connector connectable to at least one of the main module first multiple card-edge connectors, whereby, if one of the fuel-cell sensors is identified as having a loss in calibration, the software performs automatic recalibration of the one of the fuel-cell sensors that has lost calibration and disable the one of the fuel-cell sensors that cannot be automatically recalibrated.

12. The self-regulating, multi-fuel-cell breathalyzer of claim 11 further comprising a calibration gas entry in flow communication with the main air-flow channel and a regulated calibration gas source.

13. The self-regulating, multi-fuel-cell breathalyzer of claim 11 further comprising a computer connectable to the main circuit board.

14. A self-regulating, multi-fuel-cell breathalyzer, comprising:
    a) a main module with a main air-flow channel, a main circuit board with a software having first multiple card-edge connectors, an exhaust fan to pull or push fresh air through the main air-flow channel and an air-pressure sensor in flow communication with the main air-flow channel;
    b) a calibration gas entry in flow communication with the main air-flow channel and
    c) at least three fuel-cell cartridges each having a fuel-cell sensor, a pump, a fuel-cell sensor intake in flow communication with the main air-flow channel and a second multiple card-edge connector connectable to at least one of the main module first multiple card-edge connectors; and
    d) a computer connectable to the main circuit board, whereby, if one of the fuel-cell sensors is identified as having a loss in calibration, the software performs automatic recalibration of the one of the fuel-cell sensors that has lost calibration and disable the one of the fuel-cell sensors that cannot be automatically recalibrated.

* * * * *